(12) United States Patent
Moszner et al.

(10) Patent No.: US 7,495,037 B2
(45) Date of Patent: Feb. 24, 2009

(54) DENTAL COATING MATERIALS

(75) Inventors: Norbert Moszner, Eschen (LI); Simone Klapdohr, Rankweil (AT); Ulrich Salz, Lindau (DE); Jörg Zimmermann, Lustenau (DE); Volker M. Rheinberger, Vaduz (LI); Rolf Mülhaupt, Freiburg (DE)

(73) Assignee: Ivoclar Vivadent AG, Schaan (LI)

( * ) Notice: Subject to any disclaimer, the term of this patent is extended or adjusted under 35 U.S.C. 154(b) by 400 days.

(21) Appl. No.: 10/928,540

(22) Filed: Aug. 27, 2004

(65) Prior Publication Data

US 2005/0165129 A1 Jul. 28, 2005

(30) Foreign Application Priority Data

Aug. 29, 2003 (DE) ................. 103 39 912

(51) Int. Cl.
- *A61K 6/083* (2006.01)
- *A61K 6/08* (2006.01)
- *A61K 6/00* (2006.01)
- *C08F 283/12* (2006.01)

(52) U.S. Cl. ............... 523/115; 523/116; 523/118; 522/99; 522/908

(58) Field of Classification Search ........... 523/116, 523/115, 118; 522/99, 908; 526/279
See application file for complete search history.

(56) References Cited

U.S. PATENT DOCUMENTS

| 3,969,499 | A |   | 7/1976 | Lee, Jr. et al. |   |
|---|---|---|---|---|---|
| 4,324,630 | A |   | 4/1982 | Sugita et al. |   |
| 4,368,043 | A |   | 1/1983 | Yamauchi et al. |   |
| 4,648,843 | A |   | 3/1987 | Mitra |   |
| 4,883,534 | A |   | 11/1989 | Sandham et al. |   |
| 5,133,957 | A |   | 7/1992 | Suh et al. |   |
| 5,139,768 | A |   | 8/1992 | Friedman |   |
| 5,330,746 | A |   | 7/1994 | Friedman et al. |   |
| 5,403,577 | A |   | 4/1995 | Friedman |   |
| 5,644,014 | A | * | 7/1997 | Schmidt et al. | 528/43 |
| 5,914,383 | A |   | 6/1999 | Richter et al. |   |
| 6,083,421 | A |   | 7/2000 | Huang et al. |   |
| 6,191,181 | B1 |   | 2/2001 | Weikard et al. |   |
| 6,312,668 | B2 |   | 11/2001 | Mitra et al. |   |
| 6,506,816 | B1 |   | 1/2003 | Ario et al. |   |
| 6,569,917 | B1 |   | 5/2003 | Moszner et al. |   |
| 6,630,205 | B2 | * | 10/2003 | Brueck et al. | 427/387 |
| 6,649,272 | B2 | * | 11/2003 | Moore et al. | 428/447 |
| 6,794,520 | B1 |   | 9/2004 | Moszner et al. |   |
| 2002/0081385 | A1 | * | 6/2002 | Kron et al. | 427/384 |
| 2003/0224112 | A1 | * | 12/2003 | Dams | 427/372.2 |
| 2004/0039078 | A1 | * | 2/2004 | Suh et al. | 523/113 |
| 2004/0089372 | A1 | * | 5/2004 | Higgins et al. | 141/103 |
| 2005/0159504 | A1 | * | 7/2005 | Becker-Willinger et al. | 523/122 |

FOREIGN PATENT DOCUMENTS

| DE | 24 17 940 | 10/1975 |
|---|---|---|
| DE | 37 17 762 | 12/1987 |
| DE | 36 34 697 | 4/1988 |
| DE | 38 36 815 A1 | 7/1990 |
| DE | 40 11 045 C2 | 10/1991 |
| DE | 41 18 184 A1 | 12/1992 |
| DE | 41 33 494 C2 | 4/1993 |
| DE | 195 35 729 A1 | 3/1997 |
| DE | 196 13 650 C1 | 4/1997 |
| DE | 195 44 763 A1 | 6/1997 |
| DE | 197 46 708 C2 | 2/2000 |
| DE | 100 40 716 | 2/2002 |
| DE | 198 39 292 A1 | 2/2002 |
| DE | 101 06 787 A1 | 8/2002 |
| EP | 0 089 187 | 9/1983 |
| EP | 0 171 493 B1 | 2/1986 |
| EP | 0262488 A1 | 4/1988 |
| EP | 0 381 445 | 8/1990 |
| EP | 0 428 520 | 5/1991 |
| EP | 0 450 624 B1 | 10/1991 |
| EP | 0 595 840 B1 | 5/1994 |
| EP | 0 595 844 B1 | 5/1994 |
| EP | 0 716 845 | 6/1996 |
| EP | 0 897 709 | 2/1999 |
| EP | 0 900 560 | 3/1999 |
| EP | 1 070 499 A1 | 1/2001 |
| EP | 1 138 308 | 10/2001 |

(Continued)

OTHER PUBLICATIONS

Brinker et al., "Sol-Gel-Science: The Physics and Chemistry of Sol-Gel Porcessing," *Acad. Press*, Boston etc., pp. 839-880 (1990).

(Continued)

*Primary Examiner*—Mark Eashoo
*Assistant Examiner*—Michael Pepitone
(74) *Attorney, Agent, or Firm*—Nixon Peabody LLP

(57) ABSTRACT

Polymerizable materials which contain (1) 1 to 80 wt.-% of at least one polysiloxane, (2) 0.1 to 5 wt.-% of one or more initiators for radical polymerization, (3) 0 to 60 wt.-% of radically polymerizable monomer and (4) 1 to 50 wt.-% of one or more radically polymerizable monomers which carry at least phosphonic acid group, sulphonic acid group and/or mono- or dihydrogen phosphoric acid ester group, the polysiloxane (1), the monomer (3) or both being substituted by fluorine. The materials are suitable in particular for the coating of natural or artificial teeth.

22 Claims, No Drawings

FOREIGN PATENT DOCUMENTS

| | | |
|---|---|---|
| EP | 1 197 539 A2 | 4/2002 |
| EP | 1 216 681 | 6/2002 |
| EP | 1 352 936 A1 | 10/2003 |
| JP | 5-246819 A | 9/1993 |
| JP | 11-152320 A | 6/1999 |
| JP | 11-315059 A | 11/1999 |
| JP | 2000-063480 A | 2/2000 |
| JP | 2000-139960 A | 5/2000 |
| JP | 2002053806 A | 2/2002 |
| JP | 2002128621 A | 5/2002 |
| WO | WO 92/16183 | 10/1992 |
| WO | WO 93/02333 | 2/1993 |
| WO | WO 95/15740 | 6/1995 |
| WO | WO 98/48766 | 11/1998 |
| WO | WO 99/15131 | 4/1999 |
| WO | WO 99/20227 | 4/1999 |
| WO | WO 00/09030 | 2/2000 |
| WO | WO 00/69392 | 11/2000 |
| WO | WO 02/26196 | 4/2002 |
| WO | WO 03/093383 A1 * | 11/2003 |

OTHER PUBLICATIONS

Schmidt, H., "Organically Modified Silicates by the Sol-Gel Process," *Mat. Res. Soc. Symp. Proc.* 32:327-335 (1984).

Schmidt et al., "Organically Modified Ceramics and Their Applications," *J. Non-Cryst. Solids* 121:428-435 (1990).

Translation of Japan office action of Aug. 13, 2008 for JP 2004/249240.

Ep Search Report of Dec. 8, 2004.

European Office Action of Apr. 18, 2008.

Translation of Japan office action of Sep. 22, 2008, for JP 2003-035768.

European Examination Report of Oct. 28, 2008.

* cited by examiner

DENTAL COATING MATERIALS

The present invention relates to coating materials which are suitable in particular for dental purposes and can, for example, prevent the formation of plaque and the development of caries on dental substrates, in particular on natural teeth.

It is known to coat the tooth structure, above all of the tooth enamel and the dentine, for protection during dental treatment, as mechanical protection against ageing processes, for cosmetic reasons, to treat hypersensitivities or to prevent caries, gingivitis and periodontitis. For these purposes various materials are described in the state of the art.

EP 0 089 187 discloses protective varnishes which, along with vinyl acetate/vinyl chloride copolymer, contain a further copolymer which, along with vinyl acetate and vinyl chloride units, has carboxylic acid or carboxylic acid anhydride groups. The copolymers are dissolved in organic solvent.

DE 37 17 762 discloses a coating material based on polystyrene resin/rosin or rosin derivatives, dissolved in an organic solvent. The materials are provided to protect tooth surfaces against an unintentional etching.

Varnishes based on carbamide peroxide, film-formers and solvents for the brightening of teeth are known from U.S. Pat. No. 6,083,421.

WO 99/15131, EP 0 897 7099, EP 1 216 681, EP 1 138 308, EP 0 716 845 and WO 02/26196 disclose coating materials which, along with film-forming polymer and organic solvent, contain pigments such as titanium dioxide and mainly serve to provide the tooth surface with a white coating.

U.S. Pat. No. 5,133,957 discloses adhesive protective films for the desensitizing of hypersensitive teeth, based on monomer mixtures e.g. from the reaction product of N-phenylglycine or N-(p-tolyl)glycine with glycidyl methacrylate and monomers which are accessible by reacting anhydrides with hydroxyethylene methacrylate.

In U.S. Pat. No. 5,330,746, U.S. Pat. No. 5,403,577, U.S. Pat. No. 5,139,768 and EP 0 381 445 therapeutics for application to the tooth surface are described which contain strontium or potassium salts in a carrier varnish and are intended to be suitable for treating hypersensitivities in the area of the neck of the tooth.

In DE 36 34 697 a varnish for combating cariopathogenic germs such as *Streptococcus mutans* and lactobacilli is described which contains, as active ingredients, chlorhexidine digluconate and thymol and/or carvacrol.

U.S. Pat. No. 4,883,534 and EP 0 428 520 disclose varnish systems based on chlorhexidine. Moreover varnishes with other antibacterial active ingredients such as triclosan (2,4,4'-trichloro-2'-hydroxydiphenyl ether) (WO 99/20227 and WO 98/48766), cetylpyridinium chloride or benzalkonium chloride (EP 0 900 560) are known from the state of the art. These are mostly so formulated that the active ingredient is physically dissolved, in an organic solvent together with a film-forming polymer.

Fluoridation varnishes for the prevention of caries are described in U.S. Pat. No. 3,969,499, DE 24 17 940 and DE 100 40 716.

U.S. Pat. No. 4,324,630 and WO 00/09030 disclose protective varnishes which are also intended to prevent an acid attack on the tooth structure without fluoride.

Moreover coating materials based on hydrolytically condensable and radically polymerizable silanes are known. The hydrolytic condensation of these silanes leads to polysiloxanes which can be cured thermally, photochemically or by redoxinitiation via polymerizable organic groups (C. J. Brinker, G. W. Scherer, Sol-Gel-Science, Acad. Press, Boston etc. 1990, 839ff.). Inorganic/organic networks are obtained (H. Schmidt, Mat. Res. Soc. Symp. Proc. Vol. 32 (1984) 327-335; H. Schmidt, H. Wolter, J. Non-Cryst. Solids 121 (1990) 428-435).

EP 0 450 624 B1 discloses polysiloxane-containing materials which are intended to be suitable in particular for the coating of metals, plastics, paper, ceramics, wood, glass and textiles. The polysiloxanes are prepared by reaction of silanes and optionally further hydrolytically condensable compounds, for example of B, Al, P, Sn and Pb. The coating materials can moreover contain unsaturated organic compounds and can be cured by light or thermally depending on the choice of polymerization.

Similar polysiloxanes which are intended to be suitable as dental coating materials are known from DE 41 33 494 C2.

In DE 40 11 045 C2 and EP 0 107 0499 A1 varnishes for the coating of plastic substrates are described which, along with a silane with ethylenically unsaturated groups, contain a second silane with a mercapto radical. The materials are also able to be cured by UV-light without adding a photoinitiator.

DE 41 18 184 A1 discloses, coating compositions, based on fluorine-containing inorganic polycondensates which are intended to be suitable for the coating of glass, ceramic, metal, plastics and paper and are to be characterized by good anti-adhesion properties. DE 195 44 763 A1 proposes the use of these materials for the coating of braces and dentures.

According to DE 195 35 729 A1 the coating of dentures and teeth with the compositions of DE 41 18 184 A1 is intended to protect these against a colonization of their surface by microorganisms.

Coating materials are known from EP 0 171 493 B1 based on inorganic polycondensates of soluble zirconium compounds and organofunctional silanes which is intended to allow a scratch-resistant coating of plastic lenses and plastic spectacle glasses.

DE 38 36 815 A1 proposes an improvement of the materials known from EP 0 171 493 by addition of organic compounds which have functional groups which are activated only during the course of or after the end of curing, such as blocked polyisocyanates and polyesters.

Sol-gel compositions are known from EP 0 595 840 B1 and EP 0 595 844 B1, starting from non-radically polymerizable alkoxides such as e.g. tetraethoxy silane, zirconium tetra-sec.-butoxide or aluminum tri-sec.-butoxide, which, after hydrolytic condensation, are intended to be suitable for the coating of natural teeth. Curing with laser beams or gas flame is to result in glass-like coatings.

WO 92/16183 discloses compositions based on organically modified silicic acid polycondensates which are intended to be suitable for the coating of teeth and denture parts. The cured coatings are to be resistant to plaque accumulation.

WO 95/15740 and U.S. Pat. No. 6,312,668 relate to orally applicable coating materials based on polysiloxane-modified organic polymers. These are obtained by subjecting silanes with polymerizable side groups together with further components to a radical polymerization. The silanes can contain hydrolytically condensable groups which are intended to facilitate a condensation of the polymers following the polymerization. The final-curing of the materials takes place, optionally after the addition of further monomers, by renewed radical polymerization via polymerizable radicals which have remained in the polymer.

The chemical composition and the wetting behavior of the known coating materials and the natural tooth structure (enamel and dentine) clearly differ from each other. Organically modified polysiloxanes normally have hydrophobic properties, whereas the tooth structure has a hydrophilic character. Although it is known that hydrophobic coating materials are advantageous as regards the prevention of a colonization of the tooth surface by microorganisms, on the other hand they adversely effect a uniform wetting of the tooth surface and the adhesion of the materials, so that a pre-treatment of the tooth surface with acids and optionally adhesion promoters becomes necessary. The acid treatment can in turn necessitate the protection, with suitable protective coatings, of teeth that are not to be treated, which additionally increases the overall cost of the treatment.

The object of the invention is to provide coating materials which are suitable in particular for dental purposes and which show a good wetting behavior as well as a high self-adhesion, in particular to the surface of artificial and natural teeth, but which simultaneously effectively suppress the accumulation of microorganisms, in particular of plaque, and other undesired components.

According to the invention this object is achieved by polymerizable materials which contain (1) 1 to 80 wt.-%, preferably 20 to 60 wt.-% and particularly preferably 30 to 50 wt.-% of at least one polycondensate based on
  (A) one or more radically polymerizable silanes of Formula (I)

$(R^1_a\text{—}R^2)_m R^3_n SiX_{(4-m-n)}$ (I), in which $R^1$ is a radically polymerizable group, $R^2$ is absent or is a di- (a=1) or trivalent (a=2) substituted or unsubstituted hydrocarbon radical with 1 to 30 hydrocarbon atoms, the carbon chains of the hydrocarbon radical being able to be interrupted by 1 or more, preferably 1 to 5, heteroatoms, in particular O and/or S, 1 or more, preferably 1 to 5, carboxylic acid ester groups (—CO—O— or —O—CO—), carboxylic acid amide groups (—CO—NR$^7$— or —NR$^7$—CO— with $R^7$=H or $C_1$-$C_5$ alkyl), urethane groups (—HN—CO—O— or —O—CO—NH—) and/or amino groups (—NR$^8$— with $R^8$=H or $C_1$-$C_5$ alkyl), $R^3$ is $C_1$-$C_{12}$ alkyl or $C_3$-$C_{12}$ cycloalkyl, radical a $C_6$-$C_{12}$ aryl radical, $C_6$-$C_{12}$ arylalkyl or $C_6$-$C_{12}$ alkylaryl, X is halogen or a $C_1$-$C_3$ alkoxy radical, a is 1 or 2, m is an integer from 1 to 3 and n is an integer from 0 to 2, the sum of m and n being not greater than 3, and optionally
  (B) one or more silanes according to Formula (II)

$R^4_{(4-p)}SiY_p$ (II), in which $R^4$ is a $C_1$-$C_{12}$ alkyl radical or phenyl radical, which can be substituted in each case by —NH$_2$, —SH or —F, Y is halogen or a $C_1$-$C_3$ alkoxy radical- and p is an integer from 1 to 4, and/or
  (C) one or more metal compounds of Formulae, (III) and/or (IV)

$AlZ_3$ (III)

$Me(O)_r Z_s$ (IV), in which Z is halogen or a $C_1$-$C_6$ alkoxy radical, Me is zirconium or titanium r is 0 or 1, s is an integer from 1 to, 4, the sum of the valencies of the radicals O and Z corresponding to the valency of the metal, (2) 0.1 to 5 wt.-%, preferably 0.2 to 3 wt.-% and particularly preferably 0.5 to 2 wt.-% of one or more initiators for the radical polymerization and (3) 0 to 60 wt.-%, preferably 20 to 55 wt.-% particularly preferably 30 to 50 wt.-% organic, radically polymerizable monomer.

The materials are characterized in that they contain in addition (4) 1 to 50 wt.-%, preferably 5 to 30 wt.-%, particularly preferably 10 to 20 wt.-% of one or more radically polymerizable monomers of Formula (V),

$R^5_t$-Sp-A$_w$ (V), in which $R^5$ is a radically polymerizable group, t is an integer from 1 to 5, Sp is a hydrocarbon radical with 1 to 30 carbon atoms, the carbon chains of the hydrocarbon radical being able to be interrupted by O- or S-atoms, A is —PO(OH)$_2$ (phosphonic acid group), —O—PO—(OH)$_2$ (dihydrogen phosphate group), —O—PO(OH)R$^6$ (monohydrogen phosphate group) or —SO$_3$H (sulphonic acid group), $R^6$ being a branched or preferably unbranched $C_1$-$C_{20}$; preferably $C_1$-$C_{12}$, in particular $C_1$-$C_6$ alkyl radical, a $C_3$ $C_{10}$, preferably $C_6$-$C_{10}$ cycloalkyl radical or an aromatic $C_6$ $C_{20}$, preferably $C_6$-$C_{10}$ radical, $R^6$ being able to be substituted or unsubstituted, w being an integer from 1 to 3;

and that the polycondensate (1), the monomer (3) or both are substituted by fluorine.

By halogen is meant, within the framework of this invention, preferably —F, —Cl, —Br and —I. Alkyl groups can be branched or preferably unbranched. By hydrocarbon radicals which can be interrupted by heteroatoms or functional groups are meant radicals in which the heteroatoms or groups are integrated into the C—C-chains, i.e. are linked on both sides with carbon atoms. The hydrocarbon radicals can be aromatic, aliphatic or aromatic-aliphatic.

In the case of the components of the above-defined type which contain more than one group with the same name, these groups can be the same or different. For n=3 the silane (I) can carry for example 3 identical groups $R^1$ or three different groups $R^1$.

The optional substituents of the group R are preferably ester groups, in particular $C_1$-$C_6$ alkyl ester groups, $C_1$-$C_6$ alkyl or $C_1$-$C_6$ alkoxy radicals, phenyl, —Cl, —Br and —OH, the optional substituents of $R^6$ are preferably $C_1$-$C_6$ alkyl, $C_1$-$C_6$ alkoxy, halogen, preferably F, Cl or Br, or OH. If $R^6$ is an alkyl group, then this is preferably not substituted by further alkyl groups.

The materials according to the invention are suitable in particular as coating materials, in particular for natural and artificial teeth, denture parts and orthodontic devices, and are also called dental materials in the following. The dental materials can be applied intra- and extraorally.

Preferred radically polymerizable silanes of formula (I) are defined as follows:

$R^1$=a vinyl, (meth)acryl, vinylcyclopropyl, allyl or styryl group, $R^2$=dispensed with, methylene, ethylene, propylene, butylene, phenylene, —(CH$_2$)$_2$CH—O—OC—(CH$_2$)$_3$—CO—NR$^9$—(CH$_2$)$_3$— or —[CH$_2$—CHR$^9$—O—OC—(CH$_2$)$_2$—]$_2$N—(CH$_2$)$_3$— with $R^9$=H or CH$_3$, $R^3$=$C_1$-$C_{12}$ alkyl, particularly preferably $C_1$-$C_3$ alkyl, in particular methyl or ethyl;

X=F, Cl or $C_1$-$C_3$ alkoxy, particularly preferably F, methoxy or ethoxy;

n=0 or 1 m=1.

These and the following details are to be taken in each case to mean that the preferred and particularly preferred definitions of the individual variables can be chosen independently of each other. Compounds in which all the variables have one of the preferred or particularly preferred definitions are naturally quite particularly preferred.

Examples of particularly preferred silanes of Formula (I) are 3-(methacryloyloxy)-propyl-triethoxysilane, 3-(methacryloyloxy)-propyl-trimethoxysilane, 3-(acryloyloxy)propyl-methyl diethoxysilane, vinyl or allyl trimethoxysilane, or reaction products of 3-isocyanatopropyltriethoxysilane with 2-hydroxyethyl(meth)acrylate, hydroxypropyl(meth)acrylate or glycerine dimethacrylate.

Further preferred are addition products of 3-aminopropyltriethoxysilane or 3-mercaptopropyltriethoxysilane to monomers which, along with an acrylate group, contain one or more methacrylate groups, such as e.g. 2-methacryloyloxyethyl acrylate or 2-acryloyloxy-1,3-dimethacryloxy propane. Also suitable are amides which are accessible by reaction of 3-aminopropyltriethoxysilane with methacrylate carboxylic acids, e.g. reaction products of succinic acid or glutaric acid anhydride with 2-hydroxyethyl (meth)acrylate, hydroxypropyl(meth)acrylate or glycerine di(meth)acrylate.

Preferred silanes of Formula (II) are defined as follow's:
$R^4$=linear $C_1$-$C_{12}$ alkyl, particularly preferably $C_1$-$C_6$ alkyl, in particular methyl, ethyl, propyl, phenyl, the hydrogen atoms of these radicals being completely or partially replaced by F;
Y=F, methoxy or ethoxy;
p=an integer from 1 to 4', in particular 0.1 to 3.

Particularly preferred examples of silanes of Formula (II) are tetrachloro, tetraethoxy or tetramethoxysilane, $CH_3$—$SiCl_3$, $CH_3$—$Si$ $(OC_2H_5)_3$, $C_2H_5$—$SiCl_3$, $C_2H_5$—$Si$ $(OC_2H_5)_3$, phenyl-$Si(OC_2H_5)_3$, $C_3H_7$—$Si(OCH_3)_3$, $(CH_3)_2SiCl_2$, (phenyl)$_2SiCl_2$, $(CH_3)_2Si(OC_2H_5)_2$, $(C_2H_5)_3Si$—Cl, $(C_2H_5)_2Si(OC_2H_5)_2$, $(CH_3)_3Si$—Cl, $(CH_3O)_3S_1$—$C_3H_6$—$NH_2$, $(CH_3O)_3Si$—$C_3H_6$—SH, $(CH_3O)_3Si$—$C_3H_6$—$NH_2$. Silanes with p=4 are preferably used in combination with silanes in which p is 1, 2 or 3.

According to the invention polycondensates (1) are preferred which are substituted by fluorine, preferably by 3 to 22 fluorine atoms. These are preferably obtained by using as component (B) a silane of formula (II), which has fluorine substituents, these fluorine substituents being bound to the radical $R^4$. The fluorine atoms are preferably concentrated on as small as possible a number of neighboring carbon atoms. Polycondensates are particularly preferred which contain perfluoroalkyl radicals of the $C_bF_{2b+1}$- or —$C_bF_{2b}$-type, b resulting from the definition of the silanes of Formulae (I) and (II).

Preferred fluorine-substituted silanes of Formula (II) are $CF_3CH_2CH_2$—Si $(OC_2H_5)_3$, $C_2F_5$—$CH_2CH_2$—$Si(OC_2H_5)_3$, $C_4F_9CH_2C_2$—$Si(OC_2H_5)_3$, n-$C_6F_{13}CH_2CH_2$—Si $(OC_2H_5)_3$, n-$C_8F_{17}$—$CH_2CH_2$—$Si(OC_2H_5)_3$, $CF_3CH_2CH_2$—$SiCH_3$ $(OC_2H_5)_2$ and n-$C_6F_{13}CH_2CH_2$—O—CO—NH—$(CH_2)_3$—Si $(OC_2H_5)_3$.

Preferred metal compounds, of Formulae (III) and (IV), are defined as follows:
Z=$C_1$-$C_4$ alkoxy or Cl.

Particularly preferred examples of compounds of Formula (III) are $Al(OCH_3)_3$, $Al(OC_2H_5)_3$, $Al(OC_3H_7)_3$, $Al(OC_4H_9)_3$ and $AlCl_3$.

Particularly preferred metal compounds of Formula (IV) are $ZrCl_4$, $Zr(OC_2H_5)_4$, $Zr(OC_3H_7)_4$, $Zr(OC_4H_9)_4$, $ZrOCl_2$>$TiCl_4$, $Ti(OC_2H_5)_4$, $Ti(OC_3H_7)_4$ and $Ti(OC_4H_9)_4$.

The compounds of formulae (III) and (IV) can be functionalized by complex formation, for example by complexing with acids, preferably propionic acid, methacrylic acid, maleic acid or succinic acid, or β-dicarbonyl compounds, preferably acetylacetone, acetoacetic acid or 2-acetoacetoxyethyl methacrylate. During the complexing the groups Z are completely or partially displaced by the complexing groups of the complex formers.

To initiate the radical photopolymerization benzophenone, acylphosphinic oxides, such as 2,4,6-trimethyl-benzoyl-diphenyl phosphinic oxide, benzoin as well as their derivates or α-diketones or their derivates, such as 9,10-phenanthrenquinone, 1-phenyl-propane-1,2-dione, diacetyl or 4,4-dichlorobenzil are preferably used. According to a particularly preferred version camphorquinone and 2,2-methoxy-2-phenyl-acetophenone and α-diketones are used in combination with amines as reduction agent, such as e.g. 4'-(dimethylamino)-benzoic acid ester (EMBO), N,N-dimethylaminoethyl methacrylate, N,N-dimethyl-sym.-xylidine or triethanolamine.

Azo compounds such as azobis(isobutyronitrile) (AIBN) or azobis-(4-cyan-valerianic acid) or peroxides, such as dibenzoyl peroxide, dilauroyl peroxide, tert.-butyl peroctoate, tert.-butyl perbenzoate or di-(tert.butyl)-peroxide are particularly suitable as thermal initiators.

Benzopinacol and 2,2'-dialkylbenzopinacols are also suitable as initiators for hot curing.

Redox initiator combinations, such as e.g. combinations of benzoyl peroxide with N,N-dimethylsym.-xylidine or N,N-dimethyl-p-toluidine, are used as initiators for polymerization at room temperature. Moreover combinations of peroxides with such reduction agents, such as e.g. ascorbic acid, barbiturates or sulphinic acids, are also suitable.

The materials according to the invention can contain, as component (3), organic, radically polymerizable monomers, in particular one or more (meth)acrylates, (meth)acrylamides and/or pyrrolidone derivatives. Suitable for this are, in particular, monomers liquid at room temperature (diluting monomers) which have only one polymerizable group, and monomers which have two or more, preferably 2 to 5 polymerizable groups and effect a cross-linking, of the polymerizate (cross-linking monomers). Monomers, with two or more polymerizable groups are also called multifunctional monomers. Component (3) preferably contains at least one cross-linking monomer. Both diluting monomers and cross-linking monomers can be substituted by one or more, preferably 3 to 22 fluorine atoms. The use of fluorinated, i.e. fluorine-substituted, monomers is preferred, and necessary when using non-fluorinated polycondensates (1).

The fluorine atoms are also preferably concentrated on as small as possible a number of neighboring carbon atoms. Monomers are particularly preferred which contain perfluoralkyl radicals of the $C_bF_{2b+1}$- or —$C_bF_{2b}$-type, b resulting from the definition of the monomers.

Particularly preferred diluting monomers are mono(meth)acrylates, e.g. methyl, ethyl, butyl, benzyl furfuryl or phenyl (meth)acrylate and mesityl methacrylate which is characterized by a high hydrolysis stability, and 2-hydroxyethyl methacrylate (HEMA). Further preferred examples are N-monosubstituted or N-disubstituted acrylamides, such as N-ethylacrylamide, N,N-dimethacrylamide, N-(2-hydroxyethyl)acrylamide or N-methyl-(2-hydroxyethyl)acrylamide, N-monosubstituted methacrylamides, such as N-ethylmethacrylamide or N-(2-hydroxyethyl)methacrylamide, and N-vinylpyrrolidone, these compounds likewise having a high hydrolysis resistance.

Preferred cross-linking monomers are multifunctional acrylates and methacrylates, such as bisphenol-A-di(meth)acrylate, bis-GMA (an addition product of methacrylic acid and bisphenol-A-diglycidyl ether), UDMA (an addition product of 2-hydroxyethyl methacrylate and 2,2,4-hexamethylene diisocyanate), di-, tri- or tetraethylene glycol di(meth)acrylate, decanediol di(meth)acrylate, trimethylolpropane tri (meth)acrylate, pentaerythritol tetra(meth)acrylate, butanediol di(meth)acrylate, 1,10-decanediol di(meth)acrylate, 1,12 dodecanediol di(meth)acrylate, cross-linking pyrrolidones, such as 1,6-bis(3-vinyl-2-pyrrolidonyl)-hexane, and bisacrylamides, such as methylene or ethylene bisacrylamide, bismethacrylamides, such as N,N'-diethyl-1,3-bis (acrylamido)-propane, 1,3-bis (methacrylamido)-propane, 1,4-bis(acrylamido)-butane or 1,4-bis(acryloyl)-piperazine, which can be synthesized by reaction of the corresponding diamines with (meth)acrylic acid chloride or are commercially available.

Preferred fluorinated monofunctional monomers are 2,2,2-trifluoroethyl (meth)acrylate, pentafluorethyl methacrylate, 2-(pentafluorbutyl)ethyl (meth)acrylate, 2,2,3,3-tetrafluoropropyl (meth)acrylate, 3-(pentafluorobutyl)-2-hydroxypropyl (meth)acrylate, perfluorocyclohexylmethyl methacrylate, 3-(perfluorohexyl)-2-hydroxypropyl (meth) acrylate, 2-(perfluoro-3-methylbutyl)ethyl methacrylate, 3-(perfluoro-3-methylbutyl)-2-hydroxypropyl(meth)acrylate, 1H,1H,5H-octafluoropentyl(meth)acrylate, 1H,1H,2H,2H-pentafluorodecyl acrylate, 1H,1H-perfluoro-n-decyl (meth)acrylate, 2-(perfluorodecyl)ethyl(meth)acrylate, 2-(perfluoro-9-methyldecyl)ethyl (meth)acrylate, 2-perfluoro-5-methylhexyl)ethyl(meth)acrylate, 2-(perfluoro-7-methyloctyl)ethyl(meth)acrylate, 1H,1H,7H-dodecafluoroheptyl (meth)acrylate, 1H,1H-perfluoroctyl(meth)acrylate, 1H,1H,2H,2H-perfluoroctyl(meth)acrylate, 1H,1H,9H-hexadecafluorononyl(meth)acrylate and 1H,1H,1H-eicosafluoroundecyl(meth)acrylate and 1H,1H,2H,2H-pentafluorodecyl acrylate.

Preferred fluorinated cross-linking monomers are fluorinated triethylene glycol dimethacrylate (TEGDMA-F), 2,2,3,3-tetrafluoro-1,4-butanediol dimethacrylate, 1H,1H,6H,6H-perfluoro-1,6-hexanediol di(meth)acrylate, 1H,1H,10H,10H-perfluorodecanediol di(meth)acrylate, 2,2,3,3,4,4,5,5,6,6,7,7,7-dodecafluoro-1,8-octanediol di(meth)acrylate and fluorinated bis-GMA (bis-GMA-F: 2,2-bis[(4-(2-hydroxy 3-methacryloyloxy) propyloxy) phenyl]-hexafluoropropane):

$R^5$=a vinyl, (meth)acryl, (meth)arylamide, styryl group or a group of Formula (VI)

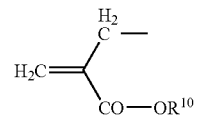

(VI)

in which $R^{10}$ is H or a branched or preferably unbranched $C_1$-$C_{20}$, preferably $C_1$-$C_{12}$, in particular $C_1$-$C_6$ alkyl radical, a $C_3$-$C_{20}$, preferably $C_3$-$C_6$ cycloalkyl radical, or an aromatic $C_6$-$C_{20}$, preferably $C_6$ $C_{10}$ radical, where $R^{10}$ can be substituted or unsubstituted;

t=1 or 2;

Sp=$C_1$-$C_{15}$ hydrocarbon radical which can be interrupted by O atoms, preferably 1 to 5 O atoms;

A=—O—P(O) (OH)$_2$, —SO$_3$H, in particular —PO(OH)$_2$;

w=1 or 2.

The optional substituents of the radical $R^{10}$ are preferably $C_1$-$C_6$ alkyl, $C_1$-$C_3$ alkoxy, halogen or OH. If $R^{10}$ is an alkyl radical, this is preferably not substituted by further alkyl radicals.

Monomers of Formula (V) are also called acid monomers in the following.

The preferred mono- and dihydrogenphosphoric acid esters capable of polymerization include 2-methacryloyloxyethyl-phenyl-hydrogen phosphate, dipentaerythritol-pentamethacryloyloxy phosphate, 10-methacryloyloxydecyl-dihydrogen phosphate, dipentaerythritol-pentamethacryloyloxy phosphate and 6-(methacrylamido) hexyldihydrogen phosphate.

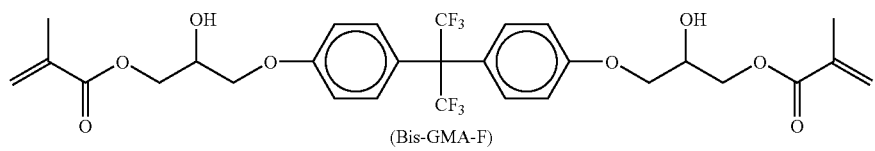

(Bis-GMA-F)

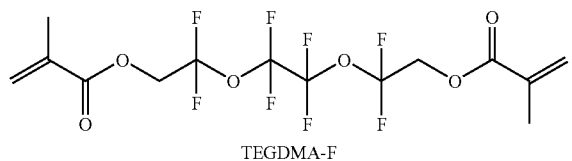

TEGDMA-F

By organic, radically polymerizable monomers (3) are meant compounds which are not silanes and do not carry any of the acid groups defined for compounds of Formula (V).

Preferred acid monomers (4) of Formula (V) are defined as follows:

$R^5_t$-Sp-A$_w$ (V)

A preferred phosphonic acid is 2-[2-dihydroxyphosphoryl)-ethoxymethyl]-acrylic acid-2,4,6-trimethyl-phenyl ester.

Preferred sulphonic acids capable of polymerization are vinylsulphonic acid, 4-vinylphenylsulphonic acid and 3-(methacrylamido)propylsulphonic acid.

Quite particularly preferred monomers of Formula (V) are the phosphonic acids vinylphosphonic acid, 4-vinylphenylphosphonic acid, 4-vinylbenzylphosphonic acid, 2-methacryloyloxyethyl phosphonic acid, 2-methacrylamidoethyl phosphonic acid, 4-methacrylamido-4-methyl-pentyl phosphonic acid 2-[4-(dihydroxyphosphoryl)-2-oxa-butyl] acrylic acid.

Polymerizable carboxylic acids, i.e. monomers which contain only a carboxyl group as acid group, are not suitable as acid monomers. According to a preferred version the dental materials according to the invention contain no polymerizable carboxylic acids, such as (meth)acrylic acid, and preferably also no non-polymerizable carboxylic acids.

The materials according to the invention can, along with the components already named, advantageously contain further components, in particular a filler (5). By adding filler, the mechanical properties of the coating can be improved. Fillers with an average particle size of 5 to 60 nm, preferably 10 to 40 nm are preferred. Unless stated otherwise, the particle size is in each case the particle size established by dynamic light scattering. Particularly preferred fillers are particulate $SiO_2$, $Al_2O_3$, $Ta_2O_5$, $Yb_2O_3$, $ZrO_2$, nanoparticulate silver, $TiO_2$ and mixed oxides Of $SiO_2$, $ZrO_2$ and/or $TiO_2$. Particularly suitable are nanoparticulate fillers with an average particle size smaller than 100 nm which are surface-modified with groups capable of polymerization and, due to their small particle size, do not reduce the transparency of the coating, i.e. do not agglomerate. A surface modification is preferably achieved in the case of siliceous fillers by silanization, and in the case of non-siliceous fillers in the way described in WO 00/69392.

The amount of filler is preferably 0 to 50 wt.-%, particularly preferably 0 to 20 wt.-% and in particular 0 to 10 wt.-%. All figures are relative to the total weight of the dental material.

Moreover the materials according to the invention can contain further additives, such as e.g. coloring agents (pigments or dyes), stabilizers, aromatics, microbiocidal active ingredients, solvents, plasticizers or UV absorbers. Preferred solvents are water, ethanol, acetone and ethyl acetate By adding volatile solvents, such as acetone or ethanol, the wetting behavior and the film formation can be positively influenced. These solvents can be used alone or in a mixture with water.

Cements and filling composites as a rule contain no solvents, adhesives and coating materials preferably 0 to 20 wt.-%, particularly preferably 0 to 10 wt.-% and more particularly preferably 0 to 5 wt.-% solvent, in each case relative to the total weight of the dental material.

According to the invention materials are particularly preferred which are comprised wholly of the components defined herein and in particular of the preferred components defined herein.

The polycondensates (1) can be obtained by hydrolytic polycondensation of components A to C in the manner described below, component (A) being able to be used alone or together with the components (B) and/or (C) for the preparation of the polycondensates. According to a preferred version mixtures are used for the preparation of the polycondensates, which along with component (A), contain at least one of components (B) or (C), preferrably (B) and (C). Particularly preferred starting mixtures for the preparation of the polycondensates contain 30 to 70 wt.-% (A) and 5 to 70 wt.-% (B), in particular 40 to 65 wt.-% (A) and 15 to 65 wt.-% (B), quite particularly preferably 45 to 60 wt.-% (A) and 20 to 60 wt.-% (B). Component (C) is, if present, preferably used in an amount of 5 to 30 wt.-%, particularly preferably 10 to 20 wt.-% (C). The amounts given relate to the total weight of the components used for the preparation of the polycondensates (1). If only silanes are used as educts, the hydrolytic condensation preferably takes place such that the compounds to be hydrolyzed are reacted, alone or in presence of solvent and optionally of a hydrolysis and condensation catalyst, with a stoichiometric amount of water or an excess of water. The reaction is carried out at room temperature accompanied by a gentle cooling or mild heating. The reaction mixture is stirred until the hydrolysis and condensation have proceeded to the desired degree of conversion, i.e. the monomer starting compounds in the reaction mixture are practically completely consumed, i.e. can no longer be detected by $^{29}$Si-NMR spectroscopy. The course of the hydrolytic condensation can be followed using $^{29}$Si-NMR spectroscopy.

If metal compounds (C), in particular compounds of Zr or Al, are used along with the silanes, the water is preferably added in portions at temperatures of $-30°$ C. to room temperature. Lower aliphatic alcohols, in particular ethanol, or isopropanol, aliphatic ketones, in particular acetone, esters, in particular ethyl acetate, ether, in particular diethyl ether or tetrahydrofuran, DMF and amines are particularly suitable as solvents. Mineral acids, in particular hydrochloric acid or hydrofluoric acid, carboxylic acids, in particular formic acids or acetic acid, sulphonic acids, phosphonic acids and phosphoric acid can be advantageously used as catalytic acids. The condensation is however preferably initiated by the acid, radically polymerizable monomers (V) alone.

Within the framework of the invention it was surprisingly found that, above all, dihydrogenphosphate esters capable of polymerization and in particular phosphonic acids not only effect a very fast hydrolytic condensation e.g. of the silanes, but at the same time promote a wetting of the tooth structure and improve the adhesion to the tooth structure.

According to a preferred version the preparation of the polycondensates (1) takes place by acidolysis of metal alkoxides, e.g. by condensation of trialkoxysilanes, tetraalkoxysilanes, titanates and zirconates accompanied by the addition of carboxylic acids, such as e.g. formic acid (cf. e.g. WO 93/2333 or DE 101 06 787 A1). During this reaction the water required for the hydrolytic condensation forms by reaction of the alkoxides with the acid accompanied by simultaneous formation of metal oxide and ester.

The preparation of the polycondensates can also alternatively take place in the presence of the other components. To this end components (A) and optionally (B) and/or (C) are mixed with radically polymerizable monomer (4) and optionally (3) solvents and filler and the condensation reaction is then initiated by adding acid and water. An initiator is then added to the polycondensate-containing mixture for the radical polymerization and cured by radical polymerization.

Depending on the type and number of hydrolyzable groups of silanes, polycondensates form which show flexible or glass like properties. The cross-linking density and thus the hardness can be increased for example by using tetraalkoxysilanes such as tetraethoxysilane. If the proportion of organic substituents is increased, for example by organically modified trialkoxysilanes or dialkoxysilanes, the network becomes increasingly more flexible, the nature and size of the organic radicals playing a role, too. Through the incorporation of Zr, Ti or Al compounds the hardness, abrasivity and refractive index of the coating can be controlled. Through cocondensation of silanes with metal alkoxides, materials with ceramic properties such as e.g. great hardness are obtained. Aluminum oxide leads, to a reduction in abrasivity, the incorporation of the elements titanium and zirconium effects an increase in the refractive index, with the result that this can be set in a targeted way by the amount of corresponding Ti and/or Zr compounds. The refractive index is moreover dependent on the porosity and crystallinity of the formed polycondensates.

Generally, the polycondensation is preferably controlled so that polycondensates liquid at room temperature are obtained as these are preferred. The homopolymerization of trialkoxysilanes results in mostly flowable products, solid products can be obtained for example by adding tetraalkoxysilanes.

After the condensation reaction is complete the polycondensates are mixed with the other components of the materials according to the invention. By polycondensates are meant condensates with more than 2, preferably more than 5 and particularly preferably more than 10 silicon, aluminum, zirconium and/or titanium atoms. The materials preferably contain no monomeric silanes or disiloxanes.

The materials according to the invention can for example be thermally or photochemically cured depending on the chosen polymerization initiator. The properties of the cured materials can be varied by different factors. The mechanical properties, such as strength and flexibility, can be controlled on the one hand by the network density of the formed condensates (high proportion of hydrolyzable groups of the compounds (A) to (C) leads to a high network density) and polymerisates (monomers with several polymerizable groups lead to a dense three-dimensional network).

The organic spacers can however also make the network more rigid or more flexible, for example through, development of hydrogen bridge bonds, variation of their length and their functional groups, which can be more or less flexible. Other properties, such as the refractive index, can be varied by the spacer groups or e.g. also by the incorporation of metal atoms, such as Zr and Ti. In the case of aliphatic spacer groups, the flexibility of the materials increases as the length of the spacer group increases, whereas the incorporation of aromatic spacer groups increases the rigidity of the cured materials. The water adsorptivity of the materials can be increased or reduced by spacers with hydrophilic or hydrophobic groups.

The properties of the coating can be further influenced by varying the cross-linking density, i.e. by changing the number of groups capable of polymerization of the silanes or of the optionally further added organic monomers.

The materials according to the invention contain at least one polycondensate or a radically polymerizable monomer which is substituted by fluorine. According to a preferred version the materials contain both a polycondensate and a radically polymerizable monomer which is substituted by fluorine. By using fluorine-containing components, in particular fluorosilanes and fluorinated monomers, a reduction of the surface energy of the materials and thus a reduction of the accumulation of plaque can be realized. Since, as a rule, these components accumulate at the boundary layer, only a comparatively small proportion of these components is necessary to achieve the desired effect. Materials which contain 5 to 10 wt.-% fluorine relative to the total weight of the cured composition are preferred.

On the other hand the fluorine-containing components endow the materials with hydrophobic properties, which clearly makes a wetting of the tooth surface difficult and adversely effects the adhesion of the materials to the tooth surface. The materials according to the invention, do not have these disadvantages. By mixing the above named components materials were successfully prepared which on the one hand effectively prevent the accumulation for example of plaque, but on the other hand show a good wetting capability for hydrophilic surfaces and good adhesion properties, i.e.

two opposite properties combine with each other. This is a surprising improvement vis-à-vis known materials.

The materials according to the invention are applied to the surface to be coated for example by spraying-on, immersion or painting, e.g. with a brush. Application can take place one or more times. When the application is repeated it is advantageous to dry the previously applied layer first, for example by evaporating off any solvent present and/or by radical polymerization, and only then apply the next layer. After application the materials are cured by radical polymerization.

The materials are suitable in particular for the coating of artificial and in particular natural teeth and denture parts. As a rule artificial teeth contain composite materials with a (meth)acrylate polymer matrix and filler, mostly based on $SiO_2$. Moreover the materials are also suitable for the coating of dental plastics, such as prosthesis plastics based on polymethyl methacrylate (PMMA), PMMA- or composite-based materials for temporary crowns and bridges, composite filling materials, composite facing and skeleton materials, orthodontic plates and activators (based on PMMA), dental metal alloys and ceramics. As long as natural, teeth are not involved, the substrates are preferably in the form of dental prostheses, such as complete or, partial prostheses, artificial teeth or orthodontic devices. Methods of coating such substrates are likewise a subject of the invention. These comprise the steps:
(i) preferably cleaning of the surface to be treated, for example by degreasing or polishing;
(ii) application of a material according to the invention;
(iii) curing of the applied material by radical polymerization;
(iv) preferably removal of the inhibition layer.

The process according to the invention is characterized in that, apart from the optional cleaning, no pre-treatment of the surface with a primer is necessary. It is particularly advantageous that, when treating natural teeth, no conditioning of the tooth surface by acid treatment and consequently no protection of tooth surfaces not to be treated with protective coatings is necessary.

By an inhibition layer is meant a thin later of uncured material which forms because atmospheric oxygen diffuses into the surface of the material, as a rule to a depth of roughly 100 μm, and inhibits the polymerization there. This inhibition layer is preferably removed with a suitable solvent, such as an alcohol, preferably an aqueous alcoholic solution, particularly preferably an ethanolic solution. The information of an inhibition layer can be prevented by suitable measures which prevent the access of oxygen to the treated surface for example by laying an oxygen-impermeable film or by working in an oxygen-free atmosphere.

The treatment of natural teeth preferably takes place in the way described in the following. The treatment can serve for therapeutic purposes, for example for the prophylactic treatment of caries or periodontitis, gingivitis, hypersensitivities, or for purely cosmetic purposes, e.g. for preventing tooth discolorations or for brightening discoloured teeth. Furthermore the treatment can serve to protect teeth during dental treatments or provide mechanical protection against ageing processes, such as abrasion and cracking. For treatments which are carried out intraorally, photochemically curable materials are preferred.

Before the application of the dental materials according to the invention, above all on areas of the tooth surface threatened by caries, such as the approximal surfaces, areas near the gingiva and exposed necks of teeth, the tooth surface is thoroughly cleaned, e.g. with a rubber cup and a cleaning paste, such as are used for professional tooth cleaning. Existing dental calculus is removed if necessary. Then residues of the cleaning paste are removed, the tooth surfaces to be treated are thoroughly rinsed with water and then dried with an air jet. A contamination of the surface by saliva is preferably prevented by introducing cotton rollers. Then the dental material is applied to the surfaces in the form of a thin layer, e.g. with a so-called microbrush, a soft brush or other suitable aids. After an action time of 10-20 seconds each coated tooth surface is irradiated for 20-40 seconds (depending on the lamp output) with a polymerization lamp common in the dental field. Then optionally further layers of the material are applied and then, after the cotton rollers are removed, rinsed once again with water.

A further subject-matter of the invention are kits which contain all the materials necessary for the application of the materials according to the invention. Kits are preferred which, along with the polymerizable material, contain an application aid, e.g. a pencil or a brush. The actual material(s) is (are) housed in suitable, i.e. preferably air- and light-tight, containers.

The invention is explained in more detail in the following using embodiments.

EXAMPLE 1

Preparation of Dental Materials Based on Fluorinated Silanes and Acid Monomers

For the preparation of the materials shown in Table 1, three solutions were prepared in each case and these were then mixed together.

Solution 1 consisted of the amounts of MEMO, PFOTEOS listed in each case and 40% of the stated amount of HEMA or MMA. In the case of samples 2 and 4 monodisperse $SiO_2$ (13 nm primary particle size), dispersed in TEGDMA, was also added as filler.

Solution 2 consisted of the amounts of BisGMA listed in each ase and 40% of the stated amount of HEMA or MMA.

Solution 3 consisted of the amounts of MA-154 listed in each ase and 20% of the amount of HEMA or MMA.

Solution 1 was mixed with solution 2, then added to solution 3 and the whole mixture was stirred for 5 mins at room temperature and for a further 2 mins at 50° C. A condensation of the silanes MEMO and PFOTEOS takes place. The condensation was carried out without water being added and relatively highly fluid varnishes were obtained. 0.5° wt. % 4-dimethylamino)-benzoic acid ester, 0.4 wt. % camphorquinone and 0.2 wt. % 2,4,6-trimethyl-benzoyldiphenyl phosphinic oxide (Lucerin TPO) were additionally added to the samples, so that the materials were able to be cured with blue light.

TABLE 1

Dental materials based on monomeric silanes and acid monomers

Composition (Figures in wt. - %)

| No. | BisGMA | MMA | HEMA | TEGDMA | MEMO | PFOTEOS | MA154 | Filler | Initiator |
|---|---|---|---|---|---|---|---|---|---|
| 1 | 21.27 | 21.27 | — | — | 20.88 | 21.24 | 14.24 | — | 1.1 |
| 2 | 15.96 | 16.18 | — | 15.37 | 15.81 | 16.08 | 11.21 | 8.29 | 1.1 |
| 3 | 22.64 | — | 20.79 | — | 20.70 | 20.96 | 13.81 | — | 1.1 |
| 4 | 16.47 | — | 16.85 | 12.48 | 15.91 | 16.12 | 12.75 | 8.32 | 1.1 |

BisGMA: 2,2-Bis-[4-(2-hydroxy-3-methacryloxy-propoxy)phenyl]propane
MMA: methyl methacrylate
HEMA: 2-hydroxyethyl-methacrylate
TEGDMA: triethylene glycol dimethacrylate
MEMO: methacryloxypropyl trimethoxysilane
PFOTEOS: tridecafluoroctyl triethoxysilane
MA154: 2-[4-(dihydroxyphosphoryl)-2-oxa-butyl]-acrylic acid

EXAMPLE 2

Preparation of a Dental Material Based on Fluorinated Silane (Comparison Example)

A dental material of the following composition was prepared This contained tridecafluoroctyl triethoxysilane (PFOTEOS) as fluorinated silane, but no acid monomer within the meaning of the invention. In spite of this, an acid monomer not according to the invention (methacrylic acid) was used. The preparation of the material took place analogously to DE 41 18 184 A1 (Example 1).

TABLE 2

Dental materials based on monomeric silane (Comparison material)

| Component | Proportion [mol] |
|---|---|
| MEMO | 0.9 |
| PFOTEOS | 0.1[1] |
| Methanol | 3.0 |
| Water | 1.6 |
| $Zr(OPr)_4$[2] | 0.1[3] |
| Methacrylic acid | 0.2 |

[1]corresponds to 10 wt. - % fluorine-containing silane
[2]70% in PrOH
[3]relative to Zr

EXAMPLE 3

Determination of the Abrasion Behavior

Cleaned, extracted bovine incisors were used for the examination of the abrasion behavior. The tooth surface was rinsed with water and dried in an air flow. Varnishes No. 1 to No. 4 were applied to the teeth and cured by being irradiated for 20 seconds with a polymerization lamp (Astralis-7). The thus-prepared incisors were then exposed to a four hour-circular toothbrush movement (bearing force 1N) in a toothbrush simulator (TBS). A dentifrice paste was used which in its scouring effect corresponded to a toothpaste cream customary in the trade (RDA 75). The wear after the simulated toothbrush treatment was ascertained analogously to the method described in DIN ISO 11609. This treatment corresponds to a tooth cleaning over a period of roughly 2 years, if it is assumed that each tooth is cleaned twice a day for 10 seconds each. In the all the examined samples the varnish layer applied to the tooth was largely worn away after 4 hours. In none of the examined samples was there however an extensive detachment of the varnish from the tooth surface. The tooth varnish adhered to the tooth surface during the total abrasion test.

EXAMPLE 4

Determination of the Adhesion to Bovine Tooth Enamel

For examining the adhesion of the materials to dentine, bovine teeth were treated with material No. 1 and the results compared with the enamel adhesion of commercially available, light-curing, single-component tooth varnishes based on multifunctional acrylates and methacrylates (Luxatemp® Glaze & Bond, DMG, Hamburg; Heliobond®, Ivoclar Vivadent AG, Liechtenstein). A polysiloxane was also prepared according to DE 41 33 494 and tested. The bovine teeth were embedded in plastic cylinders so that the dentine and the plastic were located on one plane. Then the tooth surfaces were thoroughly rinsed with water. Then a layer of material No. 1 or of the tooth varnishes customary in the trade were applied to the teeth with a microbrush, the varnish layer dried briefly, with an air jet and irradiated for 40 s with a halogen lamp (Astralis 7, Vivadent). The tooth surfaces were not conditioned with acid. A composite cylinder of Tetric® Ceram (Ivoclar Vivadent) was polymerized onto the varnish layer in two layers each of 1-2 mm. The thus-treated teeth were stored in water for 24 h at 37° C. and the shear adhesive strength was then determined according to ISO/TS11405. The measurement values found are shown in Table 3.

TABLE 3

| Adhesion to bovine tooth enamel (without acid treatment) | |
|---|---|
| Material | Adhesion value [MPa][1] |
| Material No. 1 | 5.8 ± 1.0 |
| Luxatemp ® Glaze & Bond[2] | 0.9 ± 0.9 |
| Heliobond ®[2] | 1.0 ± 1.0 |
| Example 2[2] | 2.1 ± 0.5 |

[1]Adhesive strength according to ISO/TS 11405
[2]Comparison

The adhesion values of the material according to the invention lie clearly above those of the comparison materials. The results show that, with the materials according to the invention, without additional acid treatment of the tooth surface, adhesion values can be achieved which correspond to those for glass ionomer cements which are used for example for fixing crowns.

EXAMPLE 5

Determination of the Contact Angle

To ascertain the anti-adhesion properties of the materials according to the invention the contact angle of distilled water on the film surface was measured with a contact angle measuring device (Model DAT 1100, Fibro System AB, Sweden). To this end cylindrical samples with a diameter of 20 mm and a thickness of 2 mm were prepared and exposed to light for 2×3 min (Spectramat, Ivoclar Vivadent). The non-polymerized layer on the surfaces of the samples was removed with ethanol and then 5 measurements were carried out on each sample. The average values of the measurements are given in Table 4 below. Dental coating materials customary in the trade based on a methacrylate mixture (Luxatemp® Glaze & Bond, DMG, Hamburg; Heliobond®, Ivoclar Vivadent) and a material according to Example 2 served as a comparison.

As is clear from Table 4, samples 1 to 4 show contact angles which lie well above those of the comparison materials customary in the trade. It follows from this that the surface energy and thus the danger of plaque formation for the samples 1 to 4 according to the invention is clearly less than for these comparison materials. Although the material according to Example 2 likewise produces a high contact angle, it has, as was shown above, a clearly-poorer adhesion.

TABLE 4

| Contact angles for materials according to the invention determined with distilled water | |
|---|---|
| Material | Contact angle |
| No. 1 | 94 |
| No. 2 | 90 |
| No. 3 | 94 |
| No. 4 | 90 |
| Luxatemp ® Glaze & Bond[1] | 70 |
| Heliobond ®[1] | 69 |
| Example 2[1] | 93 |

[1]Comparison

The invention claimed is:

1. Polymerizable material which contains
(1) 1 to 80 wt.-% of at least one polycondensate obtained by hydrolytic polycondensation of
   (A) one or more radically polymerizable silanes of Formula (I)

$(R^1{}_a\text{—}R^2)_m R^3{}_n SiX_{(4-m-n)}$     (I), in which $R^1$ is a radically polymerizable group, $R^2$ is absent or is a di- or trivalent, substituted or unsubstituted hydrocarbon radical with 1 to 30 carbon atoms, the carbon chains of the hydrocarbon radical being able to be interrupted by one or more heteroatoms, one or more carboxylic acid ester groups (—CO—O— or —O—CO—), carboxylic acid amide groups (—CO—NR$^7$— or —NR$^7$—CO— with $R^7$=H or $C_1$-$C_5$ alkyl), urethane groups (—HN—CO—O— or —O—CO—NH—) and/or amino groups (—NR$^8$— with $R^8$=H or $C_1$-$C_5$ alkyl), $R^3$ is a $C_1$-$C_{12}$ alkyl or $C_3$-$C_{12}$ cycloalkyl radical, $C_6$-$C_{12}$ aryl radical, $C_6$-$C_{12}$ arylalkyl, $C_6$-$C_{12}$ alkylaryl, X is halogen or a $C_1$-$C_3$ alkoxy radical, a is 1 or 2, m is an integer from 1 to 3 and n is an integer from 0 to 2, where the sum of m and n can not be greater than 3, and optionally
   (B) one or more silanes according to Formula (II)

$R^4{}_{(4-p)} SiY_p$     (II), in which $R^4$ is a $C_1$-$C_{12}$ alkyl radical or phenyl radical, which can be substituted by —F in each case, Y is halogen or a $C_1$-$C_3$ alkoxy radical, and p is an integer from 1 to 4, and/or
   (C) one or more metal compounds of Formulae (III) and/or (IV)

$AlZ_3$     (III)

$Me(O)_r Z_s$     (IV), in which Z is halogen or a $C_1$-$C_6$ alkoxy radical, Me is zirconium or titanium, r is 0 or 1, s is an integer from 1 to 4, the sum of the valencies of the radicals O and Z corresponding to the valency of the metal, (2) 0.1 to 5 wt.-% of one or more initiators for the radical polymerization and (3) 0 to 60 wt.-% further radically polymerizable monomer characterized in that the material contains in addition (4) 1 to 50 wt.-% of one or more radically polymerizable monomers of Formula (V) in monomeric form,

in which $R^5$ is a radically polymerizable group, t is an integer from 1 to 5, Sp is a hydrocarbon radical with 1 to 30 carbon atoms, the carbon chains of the hydrocarbon radical being able to be interrupted by O or S atoms, A is —PO(OH)$_2$, —O—PO(OH)$_2$, —O—PO(OH)$R^6$ or —SO$_3$H, $R^6$ being a branched or unbranched $C_1$-$C_{20}$ alkyl radical, a $C_3$-$C_{10}$ cycloalkyl radical or an aromatic $C_6$-$C_{20}$ radical, $R^6$ being able to be substituted or unsubstituted, w being an integer from 1 to 3;

and the polycondensate (1), the monomer (3) or both are substituted by fluorine.

2. Polymerizable material according to claim 1, characterized in that the polycondensate is based on at least one silane of Formula (I), in which at least one variable has one of the following meanings:

$R^1$=vinyl, (meth)acryl, vinylcyclopropyl, allyl or styryl, $R^2$=is absent, methylene, ethylene, propylene, butylene, phenylene, —(CH$_2$)$_2$CH—O—OC—(CH$_2$)$_3$—CO—NR$^9$—(CH$_2$)$_3$— or —[CH$_2$—CHR$^9$—O—OC—(CH$_2$)$_2$—]$_2$N—(CH$_2$)$_3$— with $R^9$=H or CH$_3$, $R^3$=$C_1$-$C_{12}$ alkyl, X=F, Cl or $C_1$-$C_3$ alkoxy, n=0 or 1, m=1.

3. Polymerizable material according to claim 1, characterized in that the polycondensate is based on at least one silane of Formula (II), in which at least one variable has one of the following meanings:

$R^4$=linear $C_1$-$C_{12}$ alkyl, the hydrogen atoms of $R^4$ being completely or partially replaced by F;

Y=F, methoxy or ethoxy;

p=an integer from 1 to 4.

4. Polymerizable material according to claim 1, characterized in that the polycondensate is based on at least one metal compound of Formulae (III) and/or (IV), in which Z is $C_1$-$C_4$ alkoxy or Cl.

5. Polymerizable material according to claim 1, characterized in that it contains at least one radically polymerizable monomer of Formula (V), in which at least one of the variables has one of the following meanings:

$R^5$=is a vinyl, (meth)acryl, (meth)arylamide, styryl group or a group of Formula (VI)

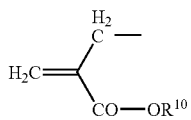

(VI)

in which $R^{10}$ is H or a branched or unbranched $C_1$-$C_{20}$ alkyl radical, a $C_3$-$C_{20}$ cycloalkyl, or an aromatic $C_6$-$C_{20}$ radical, $R^{10}$ being able to be substituted or unsubstituted;

t=1 or 2;

Sp=$C_1$-$C_{15}$ hydrocarbon radical which can be interrupted by O-atoms;

A=—O—P(O)(OH)$_2$, —SO$_3$H, —PO(OH)$_2$;

w=1 or 2.

6. Polymerizable material according to claim 1, characterized in that it additionally contains (5) 0 to 50 wt.-% filler with an average particle size of 5 to 60 nm.

7. Polymerizable material according to claim 1, characterized in that the silane of Formula (II) is substituted by fluorine.

8. Polymerizable material according to claim 1, characterized in that it contains at least one further radically polymerizable monomer (3) which is liquid at room temperature and has a radically polymerizable group.

9. Polymerizable material according to claim 1, characterized in that it contains at least one further radically polymerizable monomer (3) which has two or more radically polymerizable groups.

10. Polymerizable material according to claim 1, characterized in that it contains at least one further radical monomer (3) which is substituted by fluorine.

11. Method comprising applying a material according to claim 1 as a coating of teeth, dental prostheses or orthodontic devices.

12. Method according to claim 11, wherein the coating is applied in a manner sufficient for the preventative treatment of caries, periodontitis, gingivitis and/or hypersensitivities of teeth.

13. Method according to claim 11, wherein the coating is applied in a manner sufficient for cosmetic purposes.

14. Method for the coating of a substrate surface in which
 (i) the surface to be treated is cleaned,
 (ii) a material according to claim 1 is applied; and
 (iii) the applied material is then cured by radical polymerization.

15. Method according to claim 14, characterized in that an inhibition layer is removed following step (iii).

16. Method according to claim 14, characterized in that it does not include an acid treatment of the substrate surface.

17. Method according to claim 14, for the therapeutic or cosmetic treatment of natural or artificial teeth, wherein the substitute is a natural or artificial tooth.

18. Kit containing a material according to claim 1, the material being housed in an air- and light-tight container.

19. Kit according to claim 18, further containing an application aid for the material.

20. Polymerizable material according to claim 2, wherein $R^3$=methyl or ethyl; or X=F, methoxy or ethoxy.

21. Polymerizable material according to claim 3, wherein $R^4$=methyl, ethyl, propyl, or phenyl.

22. Polymerizable material according to claim 5, wherein $R^{10}$ is a $C_1$-$C_6$ alkyl radical; $C_3$-$C_6$ cycloalkyl, or an aromatic $C_6$-$C_{10}$ radical; or Sp=$C_1$-$C_{15}$ hydrocarbon radical which can be interrupted by 1 to 5 O-atoms.

* * * * *